United States Patent [19]
Sheridan

[11] Patent Number: 5,853,974
[45] Date of Patent: *Dec. 29, 1998

[54] ENHANCEMENT OF ALKALINE PHOSPHATASE WITH SDS IN CHEMILUMINESCENT SUBSTRATES

[75] Inventor: Patrick J. Sheridan, San Leandro, Calif.

[73] Assignee: Chiron Corporation, Emeryville, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 610,955

[22] Filed: Mar. 5, 1996

Related U.S. Application Data

[63] Continuation-in-part of Ser. No. 472,756, Jun. 7, 1995.

[51] Int. Cl.$^6$ ............... C12Q 1/00; C12Q 1/68; C12Q 1/42; C12N 9/00
[52] U.S. Cl. ............ 435/4; 435/5; 435/6; 435/21; 435/183; 252/700; 935/76; 935/77; 935/78
[58] Field of Search ............ 435/6, 4, 21; 252/700; 536/18.1; 935/76, 77, 78

[56] References Cited

U.S. PATENT DOCUMENTS

| | | | |
|---|---|---|---|
| 4,868,105 | 9/1989 | Urdea et al. | |
| 4,894,325 | 1/1990 | Englehardt et al. | |
| 4,978,614 | 12/1990 | Bronstein et al. | 435/21 |
| 5,112,960 | 5/1992 | Bronstein et al. | 536/18.1 |
| 5,124,246 | 6/1992 | Urdea et al. | |
| 5,145,772 | 9/1992 | Voyta et al. | 435/4 |
| 5,254,469 | 10/1993 | Warren | 435/188 |
| 5,451,347 | 9/1995 | Akhavan-Tafti et al. | 252/700 |
| 5,484,556 | 1/1996 | Akhavan-Tafti et al. | 252/700 |
| 5,578,253 | 11/1996 | Schaap et al. | 252/700 |

FOREIGN PATENT DOCUMENTS

| | | |
|---|---|---|
| 0254051 | 1/1988 | European Pat. Off. |
| 0 317 077 A1 | 5/1989 | European Pat. Off. |
| 0 417 841 A2 and A3 | 3/1991 | European Pat. Off. |
| 0630884 | 12/1994 | European Pat. Off. |
| WO 93/13221 | 7/1993 | WIPO |
| WO 93/13223 | 7/1993 | WIPO |
| WO 93/13227 | 7/1993 | WIPO |

OTHER PUBLICATIONS

Bublitz et al. "Heterogeneity of glycosylphosphatidylinositol–anchored alkaline phosphatase of calf intestine" *Eur. J. Biochem.* 217:199–207 (1993).

Schaap et al., "Chemical and enzymatic triggering of 1, 2–dioxetanes. 3: Alkaline phosphatase–catalyzed chemiluminescence from an aryl phosphate–substituted dioxetane" *Tet. Lett.* 27:1159–1162 (1987).

Enrico Davini et al., "Alkaline Phosphatase Inhibitors as Labels of DNA Probes," *Elsevier Science Pub. Co., Inc. GATA* 9(2):39–47, (1992).

Request for Declaration of Interference 37 C.F.R § 1.604.

Jablonski et al., "Preparation of oligodeoxynucleotide–alkaline phosphatase conjugates and their use as hybridization probes," *Nucleic Acids Res.* 14:6115–6128, (1986).

*Primary Examiner*—W. Gary Jones
*Assistant Examiner*—Ethan Whisenant
*Attorney, Agent, or Firm*—Kenneth Barovsky; Kenneth M. Goldman; Robert P. Blackburn

[57] ABSTRACT

Methods and compositions for enhancing the chemiluminescence from a stable 1,2-dioxetane triggered to produce a chemiluminescence are disclosed. Indirect, competitive nucleic acid hybridization assay formats are also described that employ these methods and compositions.

24 Claims, 6 Drawing Sheets

ENHANCEMENT OF ALKALINE PHOSPHATASE WITH SDS IN CHEMILUMINESCENT SUBSTRATES

CROSS-REFERENCE TO RELATED APPLICATIONS

This application is a continuation-in-part of U.S. patent application Ser. No. 08/472,756, filed Jun. 7, 1995, and now allowed, the disclosure of which is hereby incorporated by reference in its entirety.

TECHNICAL FIELD

This invention relates generally to analytical assays and nucleic acid chemistry and, in particular, hybridization assays. More particularly, the invention relates to methods for enhancing the sensitivity and speed of analytical assays that involve the generation of chemiluminescent signals. Furthermore, the invention related to the use of such enhancing methods to provide a nucleic acid hybridization assay having a signal with high specific activity of detection and minimum background noise. The invention also has applications in genotyping, antisense and aptamer therapeutics, mutational analysis and discontinuous probe mapping.

BACKGROUND

Nucleic acid hybridization assays are commonly used in genetic research, biomedical research and clinical diagnostics. In a basic nucleic acid hybridization assay, single-stranded analyte nucleic acid is hybridized to a labeled single-stranded nucleic acid probe and resulting labeled duplexes are detected. Variations of this basic scheme have been developed to enhance accuracy, facilitate the separation of the duplexes to be detected from extraneous materials, and/or amplify the signal that is detected.

One such assay is described in detail in commonly assigned U.S. Pat. No. 4,868,105 to Urdea et al., the disclosure of which is incorporated herein by reference. That assay involves the use of a two-part capturing system designed to bind the polynucleotide analyte to a solid support, and a two-part labeling system designed to bind a detectable label to the polynucleotide analyte to be detected or quantitated. The two-part capture system involves the use of capture probes bound to a solid support and capture extender molecules that hybridize both to a segment of the capture probes and to a segment of the polynucleotide analyte. The two-part labeling system involves the use of label extender molecules that hybridize to a segment of the polynucleotide analyte, and labeled probes that hybridize to the label extender molecules and contain or bind to a detectable label.

Alkaline phosphatase-oligonucleotide conjugates (see, e.g., EP 883096976) are often used as the signal-generating component of such hybridization assays. Adding an appropriate substrate, e.g., an enzyme-triggered dioxetane phosphate (Schaap et al. (1987) Tet. Lett. 28:1159–1162 and EPA Pub. No. 0254051) yields a detectable chemiluminescent signal. However, the background noise level may not be ideal in such assays due, in part, to the heterogeneous population of alkaline phosphatase molecules available for conjugation, which contributes to nonspecific binding of labeled probes. Low signal-to-noise ratios may also result from the preparation of alkaline phosphatase-labeled probes by conjugation of oligonucleotides to the enzyme under conditions that permit conjugation to reactive sites in or near the active site of the enzyme, thereby reducing the alkaline phosphatase specific enzyme activity.

Alkaline phosphatase is typically obtained from bovine or calf intestinal mucosa. Highly purified alkaline phosphatase can be obtained in a four-step process that yields hydrophilic and hydrophobic fractions of the enzyme (Bublitz et al. (1993) Eur. J. Biochem. 217:199–207).

Bovine or calf intestinal alkaline phosphatase can be separated into five fractions that correspond to (I) an anchorless dimer, (II) a tetramer with four glycosylphosphatidylinositol anchor molecules, (III) a tetramer as in (II) with two additional fatty acids bound to inositol on one-half of the tetramer, (IV) an octamer with two fatty acid molecules per alkaline phosphatase subunit and (V) an octamer with three fatty acid molecules per alkaline phosphatase subunit (Bublitz et al., supra). Thus, the number of alkaline phosphatase subunits, the absence or presence of glycosylphosphatidylinositol anchor molecules and the absence or presence of various numbers of fatty acid molecules per subunit contribute to the heterogeneity of the alkaline phosphatase population typically used to prepare labeled oligonucleotide probes. The hydrophobic character of the glycosylphosphatidylinositol anchor molecules and the fatty acid residues in fractions (II) through (V) are believed to contribute to the background noise in nucleic acid hybridization assays.

Unwanted background noise may result from the use of alkaline phosphatase-oligonucleotide conjugate prepared under conditions where conjugates are formed at various sites on the enzyme, including at the enzyme active site. This source of heterogeneity in the enzyme-probe conjugate population results in a label probe with less than ideal specific enzyme activity.

The lack of a homogeneous population of detectably labeled oligonucleotide probes having high specific activity of detection may limit the sensitivity and the precision of typical nucleic acid hybridization assays.

In addition, while the use of substrates such as chemiluminescent dioxetanes provides a highly sensitive means of detecting enzyme-linked assay methods, the sensitivity and speed of such assays can be increased by the use of dicationic surfactants as disclosed in EPA Publication No. 0630884, the disclosure of which is incorporated by reference herein. Such surfactants enhance the chemiluminescence produced by the decomposition of chemiluminescent compounds, for example, 1,2-dioxetanes triggered by activating agents such as enzymes.

It will be recognized by those of skill in the art that further improvements in the detectable light intensity produced by chemically triggered dioxetane chemiluminescence will provide additional advantages in assays that uses these processes.

SUMMARY OF THE INVENTION

Compositions and methods are provided for enhancing the chemiluminescence from a molecule that is capable of being activated to generate a chemiluminescent signal. Assay methods are also provided for detecting nucleic acid analytes in a sample using these compositions and methods. In general, the compositions include hydrophobic anionic chemiluminescence enhancers and the methods involve providing such enhancers in an assay or analytical technique wherein a chemiluminescent signal is generated thereby enhancing assay sensitivity and specificity. In addition, the methods for detecting nucleic acid analytes in a sample involve a solution phase hybridization assay in a competitive, indirect assay format that enables the regulation of hybridization conditions thereby enhancing assay sensitivity and specificity.

It is an object of the invention to provide a method for enhancing the chemiluminescence from a molecule that is capable of being activated to generate a chemiluminescent signal. The method involves providing a molecule that is capable of being activated to generate a chemiluminescent signal, a dicationic surfactant and a hydrophobic anionic enhancer and activating the molecule.

It another object of the invention to provide a composition that includes a molecule that is capable of being activated to generate a chemiluminescent signal, a dicationic surfactant and a hydrophobic anionic enhancer.

It is yet another object of the invention to provide an indirect, competitive nucleic acid hybridization in which "capture extender" molecules are used, that bind to "label extender" molecules that in turn bind to label probes having a detectable label bound thereto that is capable of generating a chemiluminescent signal by activating a molecule that is capable of being activated to generate a chemiluminescent signal. In a preferred format, capture extenders are bridging probes that bind to support-bound "capture probes" as well as to label extenders and a target nucleotide sequence in an analyte, and label extenders molecules are bridging probes that bind to the capture extenders as well as to "label probes," i.e., oligonucleotide segments having a detectable label bound thereto that is capable of generating a chemiluminescent signal by triggering a stable 1,2-dioxetane. In an alternate format, label extenders are bridging probes which bind to label probes as well as to capture extenders and a target nucleotide sequence in an analyte and capture extender molecules are bridging probes that bind to the label extender molecules as well as to capture probes.

It is an additional object of the invention to provide assay formats having enhanced analyte detection sensitivity and selectivity that incorporate single molecular form label probes that have enhanced specific enzyme activity and generate enhanced assay signal detection. The label probes are prepared by a method that involves purification of anchorless, hydrophilic alkaline phosphatase, conjugation of the enzyme to an oligonucleotide probe under conditions in which the enzyme active site is protected from conjugation and the conjugation of the oligonucleotide to the enzyme is site-directed, and further purification of the label probe thus prepared.

In one embodiment, the invention relates to a method for enhancing the chemiluminescence generated from a stable 1,2-dioxetane by providing a dioxetane, a dicationic surfactant and a hydrophobic anionic enhancer that has the formula $R^1X^-A^+$, wherein $R^1$ is a hydrophobic group that may be a substituted or unsubstituted hydrocarbon moiety selected from the group consisting of alkyl, cycloalkyl, alkenyl, alkynyl, aryl and aralkyl, $X^-$ is an anionic moiety covalently attached to the $R^1$ moiety, and $A^+$ is a counter-cation.

In another embodiment of the invention, a composition is provided containing a stable, 1,2-dioxetane, a dicationic surfactant and a hydrophobic anionic enhancer that has the formula $R^1X^-A^+$, wherein $R^1$ is a hydrophobic group that may be a substituted or unsubstituted hydrocarbon moiety selected from the group consisting of alkyl, cycloalkyl, alkenyl, alkynyl, aryl and aralkyl, $X^-$ is an anionic moiety covalently attached to the $R^1$ moiety, and $A^+$ is a counter-cation.

In one embodiment of the assay format, a sample containing or suspected of containing an analyte having a target nucleotide sequence is first incubated with a support-bound capture probe/capture extender hybrid complex under first hybridizing conditions. The reaction mixture thus produced, containing uncomplexed capture probe/capture extender hybrids and capture probe/capture extender/analyte complexes, is then incubated with label extender and label probe molecules under second hybridizing conditions. Complexes formed between the uncomplexed capture probe/capture extender hybrids and the label extender/label probe hybrids are then detected by detecting the chemiluminescence using the above-described method and composition for enhancing chemiluminescence. The amount of signal detected is inversely proportional to the quantity of analyte present in the sample.

In another embodiment of the assay format, a sample containing or suspected of containing an analyte containing a target nucleotide sequence is incubated with label probe/label extender hybrid complexes under first hybridizing conditions. The reaction mixture thus produced containing uncomplexed label probe/label extender hybrids and label probe/label extender/analyte complexes is then incubated with capture extender and support-bound capture probe molecules under second hybridizing conditions. Complexes formed between the uncomplexed label probe/label extender hybrids and the capture extender/capture probe hybrids are then detected using the above-described method and composition for enhancing chemiluminescence. The amount of signal detected is inversely proportional to the quantity of analyte present in the sample.

Additional objects, advantages and novel features of the invention will be set forth in part in the description which follows, and in part will become apparent to those skilled in the art upon examination of the following, or may be learned by practice of the invention.

BRIEF DESCRIPTION OF THE FIGURES

In FIG. 4B, the data are plotted on a log scale.

DETAILED DESCRIPTION OF THE INVENTION

Figure 1:
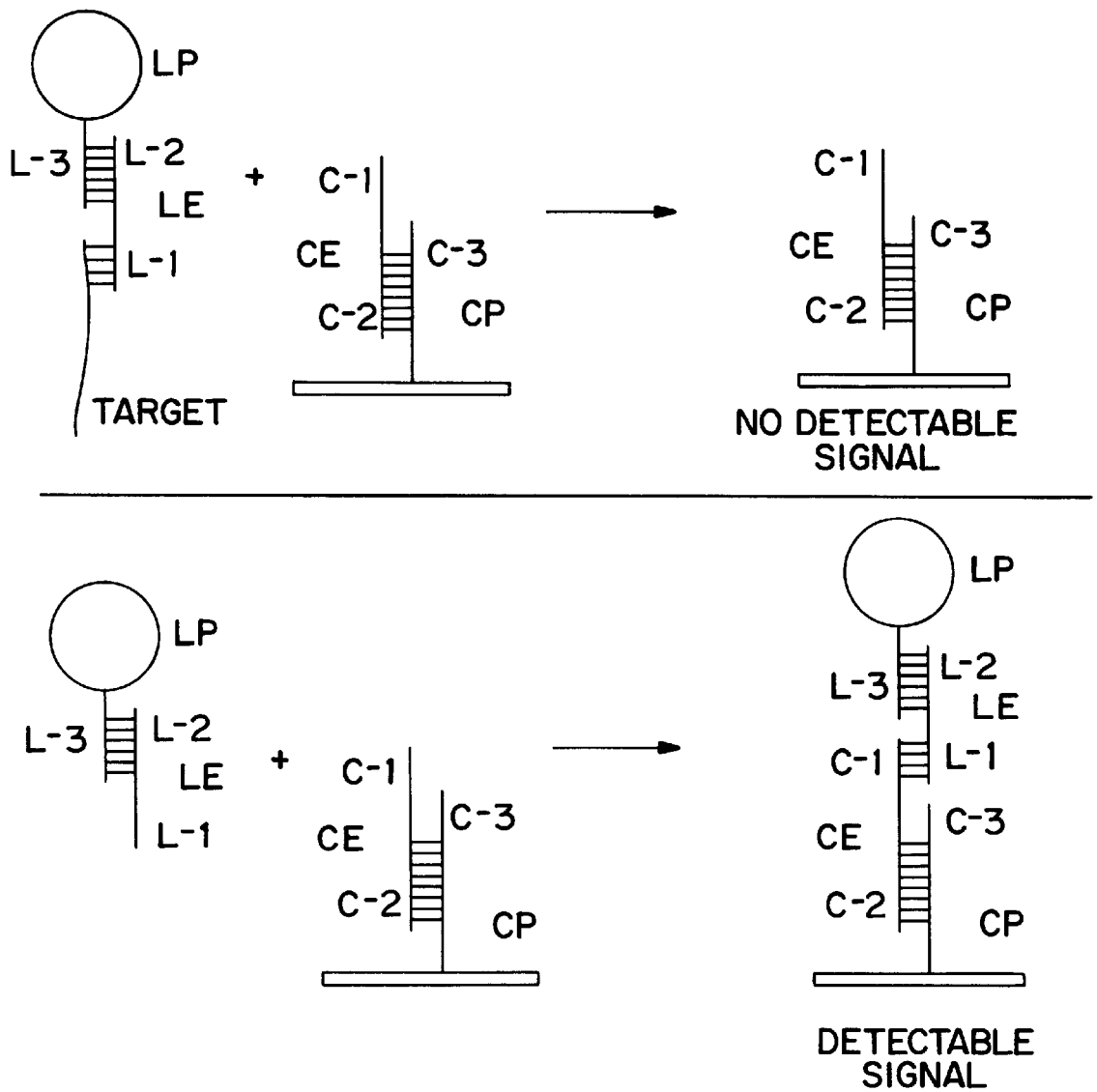
FIG. 1 is a diagram of an indirect, competitive solution phase sandwich hybridization assay format in which a sample is first incubated with a label probe/label extender hybrid complex.

Definitions and Nomenclature:

Before the present invention is disclosed and described in detail, it is to be understood that this invention is not limited to specific assay formats, materials or reagents, as such may, of course, vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "a hydrophobic group" includes two or more such hydrophobic groups, reference to "a label extender" includes mixtures of such molecules, reference to "a target nucleotide sequence" includes mixtures of two or more such sequences, and the like.

In this specification and in the claims that follow, reference will be made to a number of terms which shall be defined to have the following meanings:

As used herein, the terms "polynucleotide" and "oligonucleotide" shall be generic to polydeoxyribonucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones (e.g., protein nucleic acids and synthetic sequence-specific nucleic acid polymers commercially available from the Anti-Gene Development Group, Corvallis, Oreg., as Neugene™ polymers), providing that the polymers contain nucleobases in a configuration that allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include double- and single-stranded DNA, as well as double- and single-stranded RNA and DNA:RNA hybrids, and also include known types of modifications, for example, labels that are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties that contain not only the known purine and pyrimidine bases, but also other heterocyclic bases that have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

The term "polynucleotide analyte" refers to a single- or double-stranded nucleic acid molecule that contains a target nucleotide sequence. The analyte nucleic acids may be from a variety of sources, e.g., biological fluids or solids, food stuffs, environmental materials, etc., and may be prepared for the hybridization analysis by a variety of means, e.g., proteinase K/sodium dodecyl sulfate ("SDS"), chaotropic salts, or the like. The term "polynucleotide analyte" is used interchangeably herein with the terms "analyte," "analyte nucleic acid," "target" and "target molecule."

As used herein, the term "target region," "target sequence" or "target nucleotide sequence" refers to a probe binding region contained within the target molecule. The term "target sequence" refers to a sequence with which a probe will form a stable hybrid under desired conditions.

As used herein, the term "probe" refers to a structure comprised of a polynucleotide, as defined above, that contains a nucleotide sequence complementary to a nucleotide sequence present in the target molecule. The polynucleotide regions of probes may be composed of DNA, and/or RNA, and/or synthetic nucleotide analogs.

It will be appreciated that the binding sequences need not have perfect complementarity to provide stable hybrids. In many situations, stable hybrids will form where fewer than about 10% of the bases are mismatches, ignoring loops of four or more nucleotides. Accordingly, as used herein, the term "complementary" refers to an oligonucleotide that forms a stable duplex with its "complement" under assay conditions, generally where there is about 90% or greater homology. Typically, such complementary binding sequences will contain approximately 15 to 50, preferably 15 to 30, nucleotides.

The polynucleotides of the invention may be assembled using a combination of solid phase direct oligonucleotide synthesis and enzymatic ligation methods, as described in detail in Ser. No. 07/813,588.

An "alkaline phosphatase active site-protecting agent" refers to a compound which binds to alkaline phosphatase at the active site, thereby protecting amino acids contained in the active site from chemical modification. Such alkaline phosphatase active site-protecting agents may be alkaline phosphatase substrates such as phosphate, substrate analogues such as phosphonic acids and arsonic acid compounds, which are phosphate analogs, or other alkaline phosphatase inhibitors. Preferred alkaline phosphatase active site-protecting agents are competitive inhibitors or other compounds having reversible binding affinity for the active site of the enzyme.

As used herein, a "biological sample" refers to a sample of tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). Preferred uses of the present method are in detecting and/or quantitating polynucleotides encoding viral antigens, such as from hepatitis B virus ("HBV"), hepatitis C virus ("HCV"), hepatitis D virus ("HDV"), human immunodeficiency virus ("HIV"), and the herpes family of viruses, including herpes zoster (chicken pox), herpes simplex virus I & II, cytomegalovirus, Epstein-Barr virus, and the recently isolated Herpes VI virus, and polynucleotides encoding cell products such as cytokines.

As used herein, the term "nonspecific binding" is used to refer to those occurrences in which a polynucleotide binds to the solid support, or other assay component, through an interaction—which may be either direct or indirect—that does not involve hydrogen bonding to support-bound polynucleotides.

By "purified" or "homogeneous" is meant, when referring to a polypeptide or nucleotide sequence, that the indicated molecule is present in the substantial absence of other biological macromolecules of the same type. The term "purified" or "homogeneous" as used herein preferably means at least 90% by weight, more preferably at least 95% by weight, and most preferably at least 98% by weight, of biological macromolecules of the same type present. Thus, a "singular molecular form" of an oligonucleotide, a polypeptide or an oligonucleotide-polypeptide conjugate is a molecule that is present in purified or homogeneous form.

A "uniform population of sites" for an oligonucleotide$_n$-conjugated alkaline phosphatase means that 50%, preferably 75%, more preferably 80%, still more preferably 90%, of the oligonucleotide can be found in n tryptic fragments. For example, a uniform population of sites for an alkaline phosphatase conjugated with a single oligonucleotide is indicated by a single oligonucleotide-containing tryptic fragment of the conjugated alkaline phosphatase.

By "high specific enzyme activity" alkaline phosphatase is meant enzyme activity of at least about 2,000 to 3,000 units per mg enzyme protein. One unit of activity represents the amount of enzyme able to catalyze the conversion of 1 $\mu$mol of p-nitrophenyl phosphate to p-nitrophenol per minute in 1M diethanolamine/HCl, pH 9.8.

The term "stable 1,2-dioxetane" is intended to encompass dioxetane compounds that require the application of heat for their decomposition into two ketonic products. Chemiluminescence is "triggered" when the decomposition of a stable 1,2-dioxetane that would otherwise produce chemiluminescence upon thermal decomposition is effected by a process that does not require the use of heat. Thus, 1,2-dioxetane chemiluminescence may be triggered by the addition of base in organic solvents, by fluoride ions, or by the action of an enzyme, such as alkaline phosphatase, to catalytically convert the 1,2-dioxetane into a chemiluminescent species.

The term "alcohol" as used herein in refers to primary, secondary or tertiary alcohols, carbinols, and polyhydric alcohols wherein the substituent groups are branched or unbranched, saturated or unsaturated hydrocarbon chains containing 1 to 24 carbon atoms. The term "lower alcohol" intends an alcohol with a substituent group of one to six carbon atoms. Preferred alcohols are primary lower alcohols containing an unbranched saturated hydrocarbon substituent group.

The term "alkyl" as used herein refers to a branched or unbranched saturated hydrocarbon group of 1 to 20 carbon atoms, such as methyl, ethyl, n-propyl, isopropyl, n-butyl, isobutyl, t-butyl, octyl, decyl, tetradecyl, hexadecyl, eicosyl and the like. Preferred alkyl groups herein contain 1 to 12 carbon atoms. The term "lower alkyl" intends an alkyl group of one to six carbon atoms, preferably one to four carbon atoms. The term "cycloalkyl" intends a cyclic alkyl group, typically of 3 to 6 carbon atoms, more preferably 4 to 5 carbon atoms.

The term "alkylene" as used herein refers to a bifunctional saturated branched or unbranched hydrocarbon chain containing from 1 to 20 carbon atoms, and includes, for example, methylene (—CH$_2$—), ethylene (—CH$_2$—CH$_2$—), propylene (—CH$_2$—CH$_2$—CH$_2$—), 2-methylpropylene [—CH$_2$—CH(CH$_3$)—CH$_2$—], hexylene [—(CH$_2$)$_6$—] and the like. "Lower alkylene" refers to an alkylene group of 1 to 6, more preferably 1 to 4, carbon atoms.

The terms "alkenyl" and "alkenylene" respectively refer to a monofunction and a bifunctional branched or unbranched hydrocarbon chain containing from 2 to 24 carbon atoms and at least one double bond. "Lower alkenylene" refers to an alkenylene group of 2 to 6, more preferably 2 to 5, carbon atoms.

The terms "alkynyl" and "alkynylene" respectively refer to a monofunctional and a bifunctional branched or unbranched hydrocarbon chain containing from 2 to 20 carbon atoms and at least one triple bond. "Lower alkenylene" refers to an alkenylene group of 2 to 6, more preferably 2 to 5, carbon atoms.

The term "aryl" as used herein refers to an aromatic species containing 1 to 5 aromatic rings, either unsubstituted or substituted with 1 or more substituents typically selected from the group consisting of alkylene, alkenylene and alkynylene. The term "aralkyl" intends a moiety containing both alkyl and aryl species, typically containing less than about 20 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 20 carbon atoms in the alkylene portion and 1 to 5 aromatic rings in the aryl portion, and typically aryl-substituted alkylene.

"Optional" or "optionally" means that the subsequently described event or circumstance may or may not occur, and that the description includes instances where said event or circumstance occurs and instances where it does not. For example, the phrase "optionally washed" means that a washing step may or may not occur and that the description of the method includes both proceeding with or without a wash step.

Figure 2:
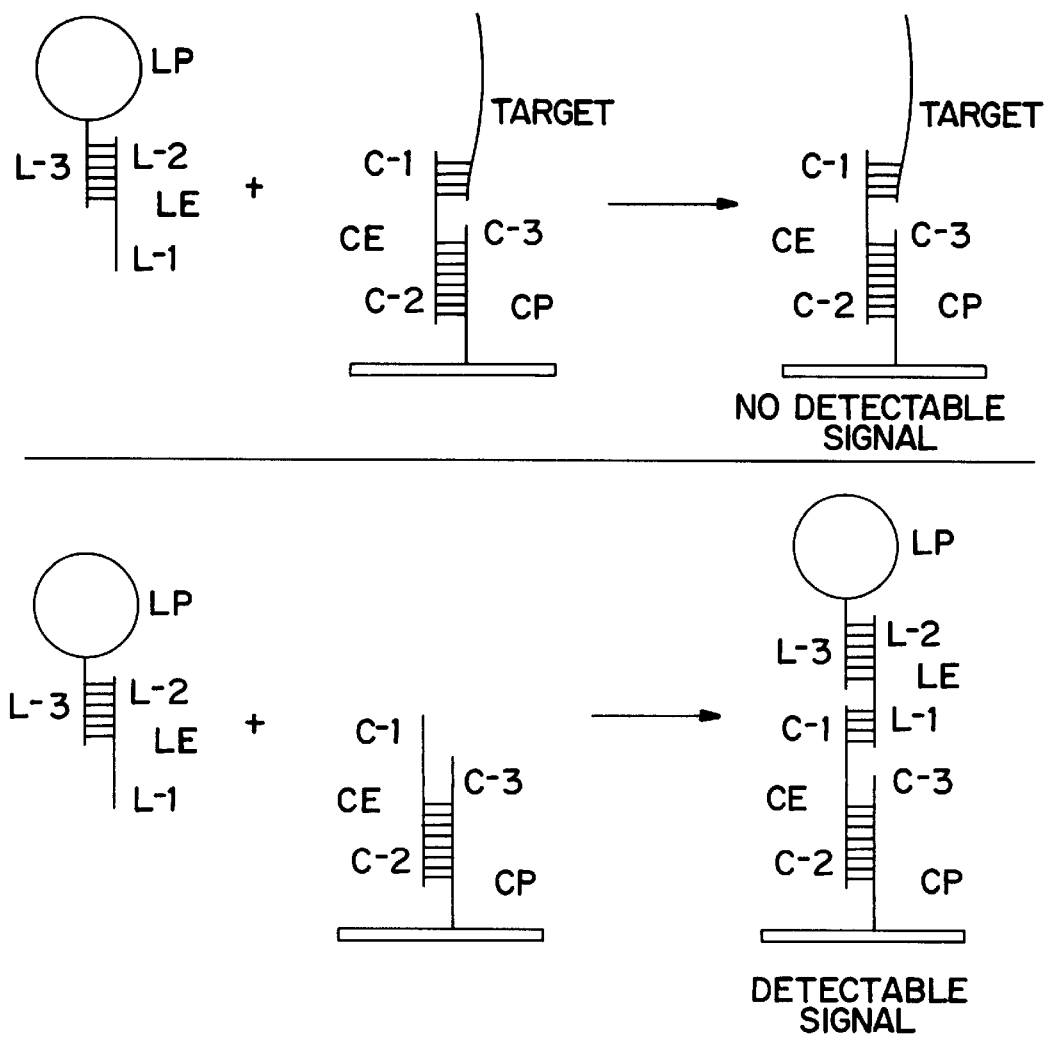
FIG. 2 illustrates an indirect, competitive solution phase sandwich hybridization assay in which a sample is first incubated with a support-bound capture probe/capture extender hybrid complex.

Referring now to the preferred embodiments represented in FIG. 1 and FIG. 2, the following terms apply to the hybridization assay depicted therein.

"Labeled probes (LPs)" are designed to bind to a label extender and contain a label moiety that is capable of generating a detectable signal. Various means for providing labels bound to a nucleic acid sequence have been reported in the literature. See, for example: Leary et al. (1983) *Proc. Natl. Acad. Sci. USA* 80:4045; Renz et al. (1984) *Nucl. Acids Res.* 12:3435; Richardson et al. (1983) *Nucl. Acids Res.* 11:6167; Smith et al. (1985) *Nucl. Acids Res.* 13:2399; Meinkoth et al. (1984) *Anal. Biochem.* 138:267; Klibanov et al. (1989) *Applied Biochem. Biotechnol.* 22:45; Grumbach et al. (1991) *J. Immunol. Meth.* 140:205; Forgac et al. (1992) *Chemicke Listy* 86:253; Sehgal et al. (1994) *Anal. Biochem.* 218:87; and Lewis et al. (1994) *Bioconjugate Chem.* 5:565. The labels may be bound either covalently or non-covalently (e.g., ionically, or through a high-affinity complex such as a biotin-avidin linkage) to the complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, $\alpha$-$\beta$-galactosidase, horseradish peroxidase, alkaline phosphatase, etc.

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels that have been employed in immunoassays and the techniques applicable to immunoassays can be employed with the subject assays.

One preferred label moiety is alkaline phosphatase. Methods of using an alkaline phosphatase substrate with alkaline phosphatase as a label moiety are known in the art (Schaap et al., Tet. Lett. 28:1159–1162 (1987) and EPA Pub. No. 0254051).

LPs comprise a region having a nucleic acid sequence L-3 complementary to a nucleic acid sequence L-2 present within a label extender and are bound to, or structured so as to bind to, a label that provides, directly or indirectly, a detectable signal. The L-3 sequence is designed to be complementary only to L-2, and vice versa, and not to sequence in any other component of the assay system. The LP may have additional non-complementary regions such as spacer regions flanking sequence L-3.

"Label probe extender molecules (LEs)," also referred to herein as "label extender molecules" or "label extenders," contain regions of complementarity with respect to the analyte polynucleotide and/or, depending on the assay format, the capture extender (L-1) and label probe (L-2). Thus, label extender molecules are single-stranded polynucleotide chains comprising a first region having a nucleic acid sequence L-1 complementary to a sequence of the analyte polynucleotide and/or a sequence of the capture extender, and a second region having a label probe recognition sequence L-2 complementary to a segment L-3 of the label probe. The LE may have additional non-complementary regions such as a spacer region between L-1 and L-2.

Depending on the assay format, "capture probe extender molecules (CEs)," also referred to herein as "capture extender molecules" or "capture extenders," bind to the analyte polynucleotide and/or to the label extender molecule and to capture probes (CPs), that are in turn bound to a solid support. Thus, capture extender molecules are single-stranded polynucleotide chains comprising a first region having a nucleic acid sequence C-1 that is complementary to a sequence of the analyte or to a sequence of the label extender, and a second, non-complementary region having a capture probe recognition sequence C-2. The CE may have additional non-complementary regions such as a spacer region between C-1 and C-2.

In the assay formats disclosed and claimed herein, either an L-1 or a C-1 nucleic acid sequence that is complementary to a nucleic acid sequence in the analyte, but not both, will be used. In either format, L-1 and C-1 are complementary nucleic acid sequences.

"Capture probes (CPs)" bind to the capture extenders and to a solid support. Thus, as illustrated in FIG. 1 and FIG. 2, capture probes comprise a first region having a nucleic acid sequence C-3 complementary to C-2 and a second region by which the CPs are covalently bound to (or capable of being covalently bound to) a solid support. The C-3 sequence is designed to be complementary only to C-2, and vice versa, and not to sequence in any other component of the assay system. The CPs may have additional non-complementary regions such as spacer regions flanking sequence C-2. Capture probes may be bound to solid supports as described in PCT Publication No. WO93/13224, the disclosure of which is incorporated by reference herein, to create a solid support for hybridization.

Generally, solution phase hybridization assays carried out using the system illustrated in FIG. 1 proceed as follows. A sample containing or suspected of containing a single-stranded nucleic acid including the target sequence is incubated under first hybridizing conditions with the label probe and label extenders. In this format, the label extender is designed to be capable of forming a bridge between the label probe and the target sequence or the capture extender. The resulting product is a mixture of nucleic acid complexes of the analyte polynucleotide bound to label probe/label extender hybrids and unbound label probe/label extender hybrids. This mixture is then added under second hybridizing conditions to a solid phase having capture extenders hybridized to capture probes bound to the surface thereof. The unbound label probe/label extender hybrid are available to hybridize to the support-bound capture probe/capture extender hybrids.

In this assay format, the presence of the target sequence in the sample depletes the population of label probes that are capable of hybridizing to the support-bound capture probe extender. Thus, the detectable signal that binds to the solid support is quantitatively related to the inverse of the amount of target sequence in the sample.

The quantity of target sequence in the sample, as reflected by the detectable signal generated as described above, may be calculated from a standard curve. A standard curve may be constructed by preparing a standard formulation containing a known quantity of an oligonucleotide comprising a nucleic acid sequence which is identical to the target sequence. A series of dilutions are made using the standard such that the quantity of oligonucleotide in the standard dilution series corresponds to the anticipated range of target sequence quantities in the sample. The standard dilution series can be used in the assay format described above to generate a series of detectable signals that correspond to the known quantities of oligonucleotide in the standard dilution series. The quantity of target sequence in the sample can then be calculated by comparing the signal generated by the sample with the signals generated by the standard dilution series.

An alternative, and preferable, assay format is diagrammed in FIG. 2. In this format, the capture extender is designed to be capable of forming a bridge between the capture probe and the target sequence of the label extender. The sample is initially incubated under first hybridizing conditions with capture extender molecules hybridized to the support-bound capture probe molecules, thereby producing a mixture of support-bound capture probe/capture extender/analyte hybrids and free capture probe/capture extender hybrids. The free capture probe/capture extender hybrids are available to hybridize with subsequently added label probe/label extender hybrid complexes. After addition of the label probe/label extender hybrid complexes the resultant mixture is incubated under second hybridizing conditions to produce detectable capture probe/capture extender/label extender/label probe hybrids and washed to remove unbound label probe/label extender hybrid complexes. The solid phase with bound detectable complexes is then separated from unbound materials, and read.

In this assay format, the presence of the target sequence in the sample depletes the population of support-bound capture extender molecules that are capable of hybridizing to the label probe/label extender hybrids. Thus, as in the format diagrammed in FIG. 1, the detectable signal that binds to the solid support is inversely related to the quantity of target sequence in the sample.

The quantity of target sequence in the sample, as reflected by the detectable signal generated as described above, may be calculated from a standard curve as described above.

Typically, the ratio of the label probe/label extender hybrid or capture probe/capture extender hybrid to anticipated moles of analyte will be greater than about 1:1, preferably at least about 10:1, more preferably at least about 25:1, and possibly as high as 100:1 or higher. Concentrations of each of the probes will generally range from about $10^{-9}$M to $10^{-6}$M, with sample nucleic acid concentrations varying from about $10^{-21}$M to about $10^{-12}$M.

Hybridization steps in the assay formats of the claimed invention are performed under appropriate stringency conditions. Stringency can be controlled by altering a parameter which is a thermodynamic variable. Such variables are well known in the art, and include formamide concentration, salt concentration, chaotropic salt concentration, pH, organic solvent content, and temperature. Preferred stringency controls are pH and salt concentration. The stringency will be varied depending on the length and nature of the target sequence.

The first hybridizing conditions in which a probe-target hybrid is formed are adjusted to provide the desired stringency for the assay. Typically, the first hybridizing conditions are high stringency conditions to increase the specificity of the probe-target hybridization reaction.

The second hybridizing conditions are used when hybrids are formed between sequences that have been designed to hybridize to each other, e.g., to form label probe/label extender or capture probe/capture extender hybrids. Accordingly, the second hybridizing conditions need not be as stringent as the first hybridizing conditions. Preferred second hybridization conditions, approximating physiological conditions, are 37° C., 0.15M monovalent cation, 16 mM $Mg^{++}$, and 1 mM spermidine.

The procedure used in the separation steps of the assay will vary depending upon the nature of the solid phase. For particles, centrifugation or filtration will provide for separation of the particles, discarding the supernatant or isolating the supernatant. Where the particles are assayed, the particles will be washed thoroughly, usually from one to five times, with an appropriate buffered medium, e.g., phosphate buffered saline (PBS) containing a detergent such as SDS. When the separation means is a wall or support, the supernatant may be isolated or discarded and the wall washed in the same manner as indicated for the particles.

An additional focus of the present invention is to enhance both assay specificity by decreasing nonspecific binding, and assay sensitivity, i.e., the ability to distinguish between different nucleic acid sequences. These aims are achieved, in part, by providing a homogeneous population of label probes having high specific activity of label detection.

Preparing such label probes involves, at the outset, providing purified, hydrophilic alkaline phosphatase molecules having high specific enzyme activity. The purified alkaline phosphatase is then conjugated to an oligonucleotide probe containing the L-3 nucleic acid sequence under conditions which control the sites on the enzyme that are available for conjugation. Optionally, the alkaline phosphatase-oligonucleotide conjugate thus formed may be further purified.

A purified hydrophilic alkaline phosphatase preparation may be made using the procedures of Bublitz et al., supra, the disclosure of which is incorporated herein by reference. Bublitz et al. reported that even though a typical alkaline phosphatase preparation may be enzymatically 99% pure, it may consist of more than one fraction of enzyme. Thus, a hydrophilic, anchorless alkaline phosphatase dimer may be prepared from bovine or calf intestinal mucosa or chyme by extracting with a lower alcohol such as butanol, purifying the enzyme by immunoaffinity chromatography and separating the anchorless, hydrophilic dimer fraction from the glycosyl-phosphatidylinositol-alkaline phosphatase fraction by hydrophobic interaction chromatography, for example, using a phenyl Sepharose® column. Anchorless, hydrophilic alkaline phosphatase dimer can also be prepared from the glycosylphosphatidylinositol-alkaline phosphatase fraction by treatment with phosphatidyl-inositol-specific phospholipase C or glycosylphosphatidy-linositol phospholipase D followed by separation of hydrophilic and hydrophobic fractions by reverse phase chromatography (e.g., octyl Sepharose®).

Alkaline phosphatase may also be obtained and purified from other sources and species including bovine liver, placenta, and kidney, porcine intestinal mucosa, placenta, and kidney, ovine intestinal mucosa, as well as from bacteria such as *Escherichia coli*.

The preparation of label probes with high specific activity of detection involves conjugation of a highly purified oligonucleotide ester to reactive amines on alkaline phosphatase in the presence of a molecule which protects the enzyme active site from conjugation. Thus, during the conjugation reaction, the enzyme active site may be protected by co-incubation with enzyme substrates, for example, phosphates, substrate analogues, or inhibitors, such as phosphonic acids. Techniques for the preparation and purification of oligonucleotide esters are well known in the art. See, for example, Moller et al. (1995) *Bioconjugate Chem.* 6:174 and Ivanovskaya et al. (1994) *Molecular Biol.* 28:754.

Preferably, the alkaline phosphatase-oligonucleotide conjugate is made using modifications of the methods described in U.S. Pat. No. 4,868,105 to Urdea et al., supra, and Urdea et al. (1988) *Nucl. Acids Res.* 16:4937–4955, the disclosure of which is incorporated herein by reference.

The method generally involves a first step of reacting the crosslinker with the oligonucleotide to produce an "activated" oligonucleotide. In particular, water-soluble crosslinking agents are preferred, for example, bis (sulfosuccinimidyl)suberate. The ratio of crosslinker to oligonucleotide may be varied independently to optimize the reaction product. In general, the crosslinker may be present in excess sufficient to avoid the formation of crosslinked oligonucleotide dimers. Accordingly, the crosslinker:oligonucleotide ratio will be in the range of about 5 to 100, preferably about 5 to 25, and most preferably 5 to 10.

The preparation of a homogeneous population of label probes involves the next step of conjugating the alkaline phosphatase to the activated oligonucleotide under conditions wherein the reactivity of the amines on the enzyme can be modulated to direct the conjugation to a uniform population of reactive sites in the enzyme. Due to the microenvironments of amine groups in alkaline phosphatase, the reactivity of the amines may be controlled by varying the pH of the conjugation reaction conditions, thereby directing the conjugation to a uniform population of reactive sites. In addition, the ratio of the activated oligonucleotide to alkaline phosphatase may be varied between 5 and 100 or higher. This yields a label probe in which an oligonucleotide is conjugated to a uniform population of amines.

The pH of the conjugation reaction may be varied to yield an enzyme-oligonucleotide conjugate having desired (e.g., maximum) enzyme activity by altering the buffer composition of the reaction solution. For example, in order to buffer the conjugation reaction in the appropriate range of physiological pH, i.e., in the range of about pH 6.6 to pH 8.0, more typically in the range of about pH 7.2 to pH 7.8, a phosphate buffer may be used. Phosphate, as an alkaline phosphatase substrate, provides protection of the enzyme active site. Alternative buffering compositions capable of providing a reaction mixture at a desired pH are well known in the art and may be found in, for example, the *CRC Handbook of Chemistry and Physics,* D. R. Lide, ed., 1994. Differential reactivity of protein amine groups as a function of pH in reactions using crosslinking agents has been reported by Grumbach et al., supra. The differential pH dependence of hydrolysis and aminolysis reactions of crosslinking agents with proteins has been described by Anjaneyulu et al. (1987) *Int. J. Peptide Protein Res.* 30:117–124.

The ratio of oligonucleotide to alkaline phosphatase in the label probe (i.e., the number of conjugated sites on the enzyme) may be determined by analytical gel electrophoresis using techniques well known in the art. In addition, the population of alkaline phosphatase sites conjugated to oligonucleotides can be determined digesting the oligonucleotide-conjugated enzyme and performing amino acid analysis on the digest using techniques well known in the art. Enzyme activity of the label probe may be determined and compared to the enzyme activity of the purified alkaline phosphatase. High specific activity label probes, preferably having 75% to 100%, more preferably 80% to 100%, and most preferably 90% to 100% of the enzyme activity of the starting materials are then used in nucleic acid hybridization assays.

Optionally, the label probe may be further purified using ion exchange chromatography, hydrophobic interaction chromatography (e.g., phenyl Sepharose®), reverse phase chromatography (e.g., octyl Sepharose®), chromatofodusing, or the like. Alternatively, and in general preferably, the label probe is further purified using affinity chromatography as described, for example, in Landt et al. (1978) *Biochem.* 17:915–919, the disclosure of which is incorporated herein by reference. Affinity chromatography using alkaline phosphatase substrates or substrate analogues has the added benefit of providing label probes which have intact alkaline phosphatase binding sites.

This procedure may be used to provide high specific-activity label probes for use in virtually any type of hybridization assay wherein label probe molecules are used, including a wide range of solution phase hybridization assays, amplification assays, filter hybridization methods, assays involving the polymerase chain reaction ("PCR"), and the like. One example of a hybridization assay with which the present technique is useful is that described in U.S. Pat. No. 4,868,105 to Urdea et al., or, preferably, that described above in conjunction with the configuration illustrated in FIG. 1 and FIG. 2 and described above.

A substrate composition for alkaline phosphatase includes a chemiluminescent stable 1,2-dioxetane; such chemiluminescent compounds are well known in the art (see, e.g., U.S. Pat. No. 5,145,772 to Voyta et al. and European Patent Publication No. 0630884). A preferred substrate composition includes an enzyme-triggered dioxetane phosphate. A more preferred substrate composition includes dioxetane phosphate in the presence of a dicationic surfactant for enhancing the chemiluminescence of dioxetanes, most preferred is a dioxetane in the presence of a dicationic surfactant and a hydrophobic anionic chemiluminescent enhancer.

As disclosed in EPA Publication No. 0630884, a preferred dicationic surfactant has the structural formula $Z^-(R^2)_3B^+$-$CH_2$-Y-$CH_2B^+(R^3)_3Z^-$ wherein B may be phosphorus, nitrogen or a combination thereof, Z is an anionic counterion and $R^2$ and $R^3$, which may be the same or different, and may be unsubstituted or substituted alkyl or aralkyl containing 1 to 20 carbon atoms and Y may be a dialkylenearyl, aryl, alkylene, alkenylene and alkynylene containing 4 to 20 carbon atoms.

Preferred dicationic surfactants that may be used to amplify the chemiluminescence from triggered 1,2-dioxetane reactions include those having the following structure:

wherein the $X^-(R^3)_3A^+CH_2$- substituent on the benzene ring may be in ortho, meta, or para position, A may be phosphorus or nitrogen, $R^2$ and $R^3$ may be alkyl or aralkyl containing about 1 to about 20 carbon atoms and $X^-$ is a fluoride, chloride, bromide or iodide. More preferably, the dicationic surfactant is 1-(tri-n-octylphosphoniummethyl)-4-(tri-n-butylphosphonium-methyl)benzene dichloride:

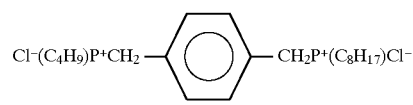

which may be prepared by reacting 4-(chloromethyl)benzyl tri-n-butylphosphonium chloride with tri-n-octylphosphine as described in EPA Publication No. 0630884.

These surfactants are typically used in combination with stable 1,2-dioxetanes that can be triggered by chemical reagents, e.g., acids, bases, salts, enzymes, inorganic and organic catalysts and electron donors, to generate chemiluminescence. Such stable dioxetanes are well known in the art and preferred dioxetanes are disclosed in EPA Publication No. 0630884. Amplification of the chemiluminescence by the surfactants may be observed with surfactant concentrations between about 0.001% and about 10%, preferably between about 0.01% and about 0.5%.

Hydrophobic anionic chemiluminescence enhancer may be of the formula $R^1X^-A^+$, wherein $R^1$ is a hydrophobic group that may be a substituted or unsubstituted hydrocarbon moiety having between about 1 to 20 carbon atoms, preferably about 4 to 18 carbon atoms, more preferably about 6 to 18 carbon atoms, including alkyl, cycloalkyl, alkenyl, alkynyl, aryl, aralkyl and similar such functional groups. $X^-$ is an anionic moiety covalently attached to the $R^1$ moiety. $X^-$ may be sulfate, sulfite, sulfonate, acetate, butyrate, phosphate, phosphite, phosphonate, carbonate, carboxylate, arsenate, and the like. $A^+$ is a countercation that may be sodium, potassium, silver, ammonium, Group IA alkali metal cations, other monovalent metal cation, and the like. Preferred hydrophobic anionic chemiluminescent enhancers include an alkyl or aralkyl group that provides a hydrophobic component and an anionic group. In addition, the enhancer may include a cationic moiety, such as ammonio, amino and the like, thereby providing a hydrophobic zwitterionic enhancer. Examples of such hydrophobic anionic enhancers, and commercial sources from which they may be obtained, include 3-[(3-cholamidopropyl)-dimethylammonio]-2-hydroxypropanesulfonate ("CHAPSO"; Sigma), 2-[N-cyclohexylamino)ethane-sulfonate ("CHES"; Sigma), 4-phenylbutyrate ("4-PBA";

Aldrich), chenodeoxycholate ("CDC"; Sigma), taurodehydrocholate ("TDHC"; Calbiochem), taurolithocholate ("TLCA"; Sigma), deoxycholate ("DC"; Sigma), 4-sulfobenzoate ("4-SBA"; Aldrich), cholate ("CA"; Sigma), hexane sulfonate ("HSA"; Sigma), taurocholate ("TCA"; Sigma), glycocholate ("GCA"; Sigma), glycodeoxycholate ("GDCA"; Sigma), benzene sulfonate ("BSA"; Sigma), tauroursodeoxycholate ("TSDC"; Sigma), taurodeoxycholate ("TDC"; Sigma), p-toluene sulfonate ("PTSA"; Sigma), taurochenodeoxycholate ("TCDC"; Sigma) and sodium dodecyl sulfate ("SDS"; Sigma).

By including a hydrophobic anionic enhancer in a reaction wherein dioxetane chemiluminescence is generated in the presence of a dicationic surfactant, the chemiluminescence in increased over the chemiluminescence produced by the dioxetane in the presence of a surfactant in the absence of the enhancing agent, as shown in Table 1.

TABLE 1

PEAK ENHANCEMENT OF CHEMILUMINESCENCE

| COMPOUND | RELATIVE CHEMILUMINESCENT INTENSITY | CONCENTRATION % (w/w) |
| --- | --- | --- |
| (no enhancer) | 1.00 | |
| CHAPSO | 2.37 | 0.25 |
| CHES | 3.24 | 0.25 |
| 4-PBA | 3.42 | 0.25 |
| CDC | 4.73 | 0.0625 |
| TDHC | 5.81 | 0.25 |
| TLCA | 6.39 | 0.25 |
| DC | 6.84 | 0.125 |
| 4-SBA | 7.34 | 0.125 |
| CA | 8.17 | 0.125 |
| HSA | 8.85 | 0.125 |
| TCA | 9.28 | 0.125 |
| GCA | 9.36 | 0.125 |
| GDCA | 10.55 | 0.0625 |
| BSA | 12.23 | 0.25 |
| TSDC | 12.92 | 0.125 |
| TDC | 14.90 | 0.125 |
| PTSA | 16.75 | 0.125 |
| TCDC | 19.88 | 0.125 |
| SDS | 23.02 | 0.0625 |

Figure 4A:
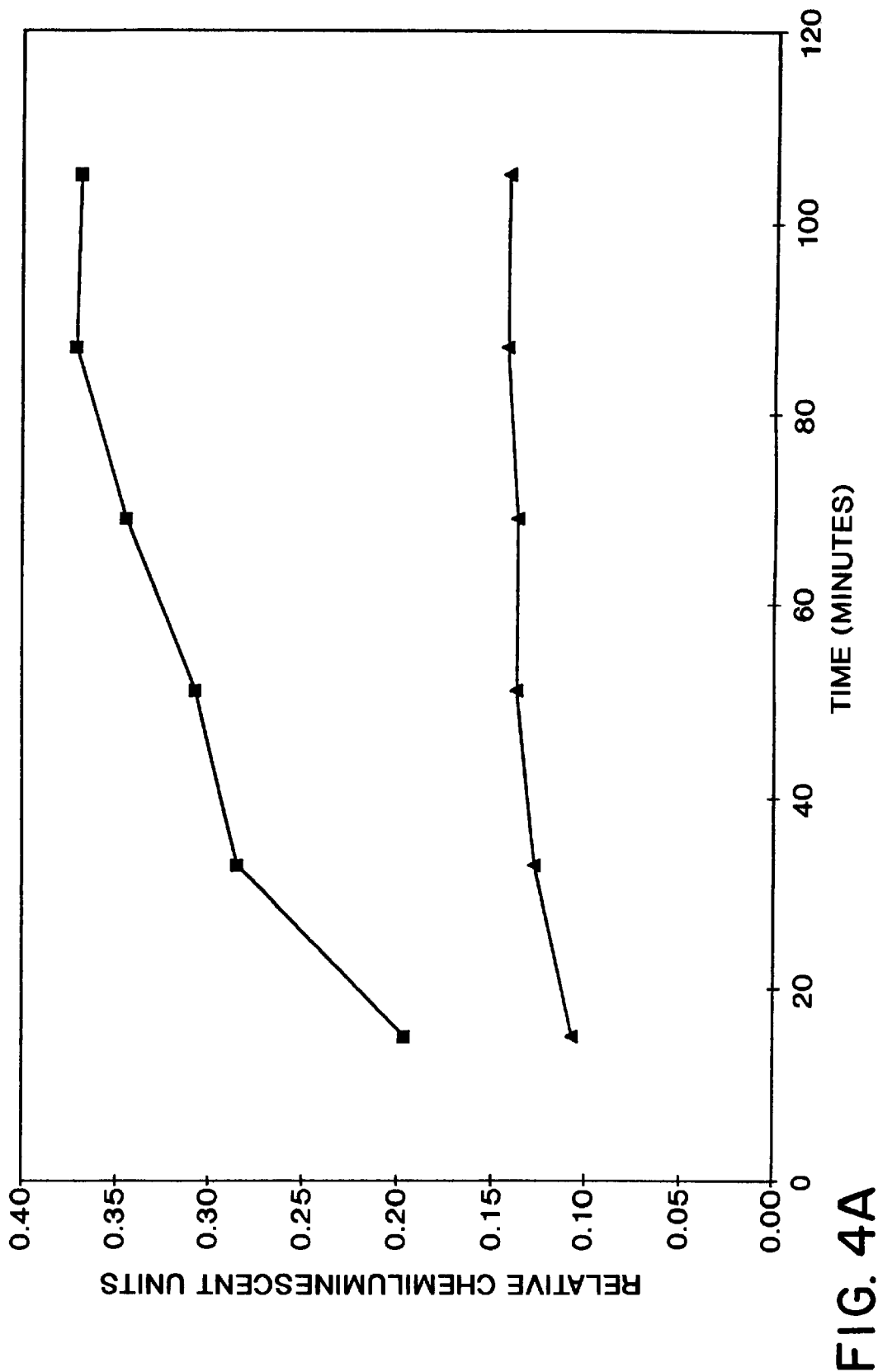
FIG. 4A is a graph depicting the effect of the hydrophobic anionic enhancer sodium dodecyl sulfate on the background chemiluminescence generated in the absence (solid triangles) or presence (solid squares) of the enhancer in a soluble alkaline phosphatase assay.
Figure 4B:
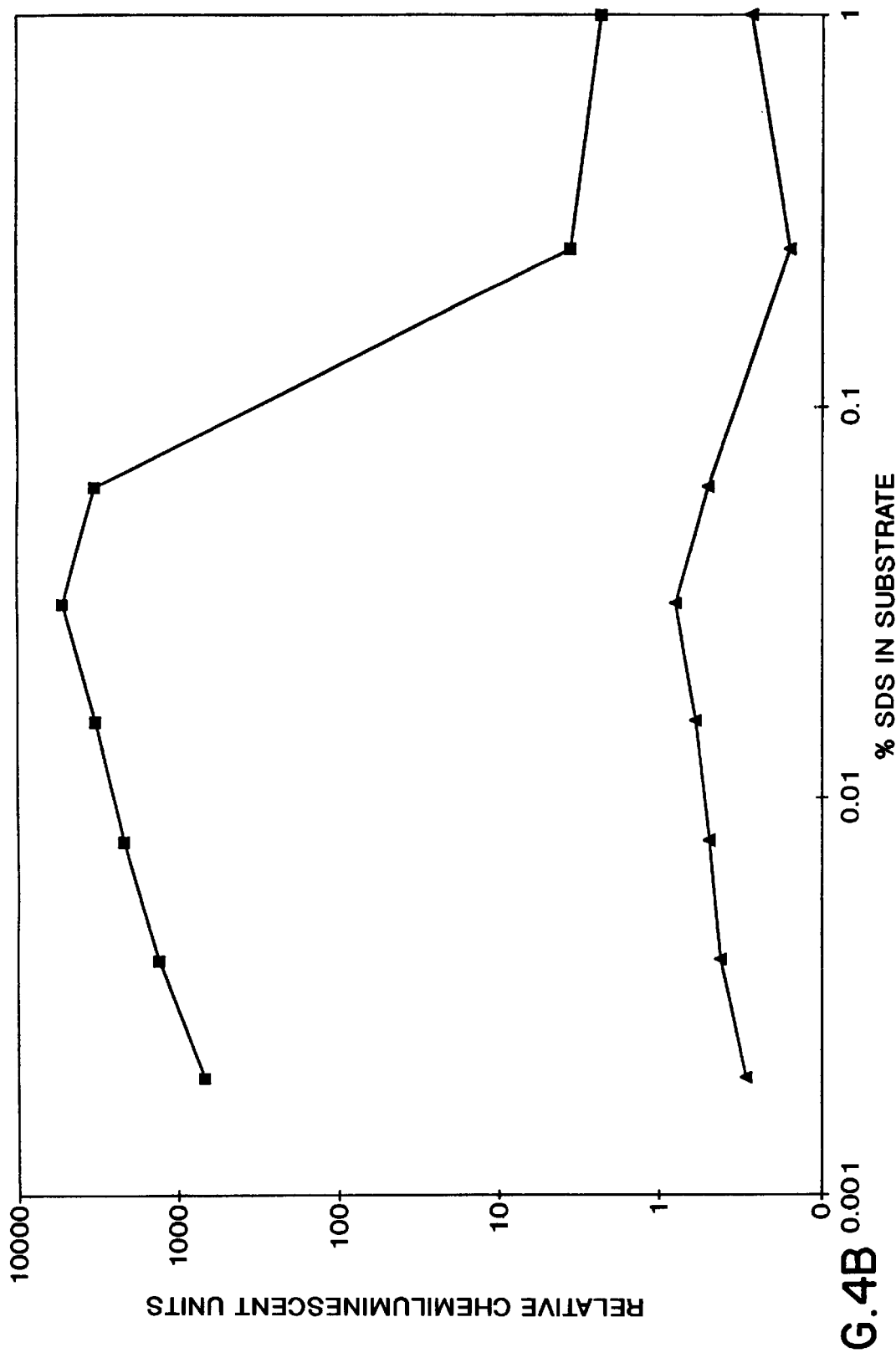
FIG. 4B is a graph showing the effect of sodium dodecyl sulfate on chemiluminescence generated in the absence (solid triangles) and presence (solid squares) of soluble alkaline phosphatase.

The hydrophobic anionic enhancers increase the relative light intensity of 1,2-dioxetane chemiluminescence without increasing the background level of light generation (see, FIG. 4A and FIG. 4B). The concentration of enhancer added to a chemiluminescent reaction depends on the concentration of dioxetane and surfactant. For example, in an enzyme-catalyzed reaction (e.g., alkaline phosphatase), the concentration of dioxetane phosphate is adjusted so that the enzyme is fully saturated. Thus, the concentration of dioxetane can be in the range of about 2- to 10-fold greater than the $K_m$ of the enzyme, or higher depending on the solubility of the dioxetane. The weight ratio of surfactant to dioxetane can be between about 0.1:1 and about 100:1, preferably between about 1:1 and 20:1. Finally, molar ratio of the hydrophobic anionic enhancer to surfactant can be between about 0.1:1 to 10:1, preferably between about 0.5:1 to about 3:1 and more preferably between about 0.5:1 and 1.5:1.

Accordingly, the present invention relates to an improved method for detecting chemiluminescence in solution phase nucleic acid hybridization assays wherein label probes carrying alkaline phosphatase are used, as described below in detail and exemplified herein in Examples 1 and 5. In addition, it will be clear to those of ordinary skill in the art that the hydrophobic anionic enhancer compositions and methods of the present invention may find use as in other procedures that employ surfactant-enhanced chemiluminescent assays. Examples of such assays include enzyme-linked immunoabsorbent assays (ELISAs), Western blotting, Southern blotting, other assays that use alkaline phosphatase-based detection systems, and the like.

The invention also provides novel assays that are specific (e.g., able to recognize single nucleotide differences between analyte nucleic acid sequences), sensitive (e.g., able to quantitate attomole amounts of analyte nucleic acids) and easily automated. Thus, the invention is particularly useful in blood screening assays and genotype or subtype assays. The invention is particularly suitable for mutational analysis of genomic DNA or RNA and other structural analyses of nucleic acids. In addition, the invention may be used to monitor gene therapy or anti-sense drugs and for mapping discontinuous probes that bind tightly to nucleic acid targets for use in diagnostics or as antisense therapeutics as described in commonly assigned U.S. patent application Ser. No. 08/349,316 to Collins, filed Dec. 5, 1994, entitled "Discontinuous Probe Design Using Hybritope Mapping."

Experimental

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, *Molecular Cloning: A Laboratory Manual,* Second Edition (1989); *Oligonucleotide Synthesis* (M. J. Gait, ed., 1984); *Nucleic Acid Hybridization* (B. D. Hames & S. J. Higgins, eds., 1984); and a series, *Methods in Enzymology* (Academic Press, Inc.). All patents, patent applications, and publications mentioned herein, both supra and infra, are hereby incorporated by reference.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

In Examples 1 and 5, an oligonucleotide marked with a superscript "c" denotes an oligonucleotide which is complementary to the oligonucleotide not so marked. Thus, "target$^c$" is an oligonucleotide which contains a target sequence which is complementary to "target." An oligonucleotide marked with a superscript "c'" denotes an oligonucleotide which is complementary to an oligonucleotide marked with a superscript "c." Thus, "target$^{c'}$" denotes an oligonucleotide which contains a nucleic acid sequence which is complementary to "target$^c$".

EXAMPLE 1

Preparation of Alkaline Phosphatase and Alkaline Phosphatase-Labelled Probe

Oligonucleotide probes were prepared using an anchorless, hydrophobic preparation of alkaline phosphatase. The process of conjugating the oligonucleotide probe was conducted under conditions which selectively direct the conjugation to a uniform population of sites on the enzyme and in the presence of phosphate to insure that the active site on the enzyme will not be available for conjugation. A homogeneous population of alkaline phosphatase-oligonucleotide conjugates was produced after further purification of the conjugate using additional chromatography steps.

A. Purification of Alkaline Phosphatase. Alkaline phosphatase was purified from a commercially available source to produce an anchorless, hydrophilic preparation as follows.

An alkaline phosphatase affinity column was prepared according to the method of Landt et al., supra. The column was poured using approximately 1 ml of L-histidyldiazobenzylphosphonic acid resin suspension (Sigma) per mg of alkaline phosphatase. The poured column was packed by running 10 mM Tris HCl, pH 8.0, through at a rate of about 10–20 ml/hr. The optical density of the column effluent was monitored at 280 nm until the $OD_{280}$ was approximately 0.00.

Washed and concentrated soluble alkaline phosphatase was prepared as follows. Alkaline phosphatase (Boehringer Mannheim) was concentrated, and the buffer in which the enzyme was originally supplied was exchanged for 10 mM Tris HCl, pH 8.0, in a Centricon-30 (Amicon) concentrator that had been rinsed with 10 mM Tris HCl, pH 8.0. The enzyme and 10 mM Tris HCl, pH 8.0, were added and the concentrator was centrifuged at 3000–4000×g. This process was repeated twice.

The washed, concentrated alkaline phosphatase was applied to the packed column at a rate of 10–20 ml/hr. The column was washed using 10 mM Tris HCl to remove impurities which do not specifically bind to the resin. The retained alkaline phosphatase was eluted by 10 mm $Na_2HPO_4$ in 10 mM Tris HCl, pH 8.0.

Collected fractions containing alkaline phosphatase was concentrated using a Centriprep-30 (Amicon) or Centricon-30, or both, as described above. The concentrated alkaline phosphatase was washed into 100 mM phosphate buffer, pH 7.2, at 4° C. or alkaline phosphatase storage buffer containing 3M sodium chloride, 1 mM magnesium chloride, 0.1 mM zinc chloride, 30 mM triethylamine, pH 7.4.

B. Conjugation of alkaline phosphatase to an oligonucleotide probe to form the label probe. The 3'-long chain amine ("LCA") portion (X) of the bla3 oligonucleotide (5'-AAGTACGACAACCACATCX-3') (SEQ ID NO:1), wherein X is is $N^4$-(6-aminocaproyl-2-aminoethyl)-cytosine, is activated using bis(sulfosuccinimidyl)suberate ("$BS^3$") (Pierce) in a 1:10 ratio of bla3:$BS^3$. Thus, $BS^3$ (21.5 mg) and bla3 (274 nmoles/ml) are added to 100 mM phosphate buffer, pH 7.8, and incubated for 30 min at room temperature.

The reaction mixture is applied to a NAP-5 column (Pharmacia) previously equilibrated with 100 mM phosphate buffer, pH 6.5, at 4° C. The desired product is eluted using 100 mM phosphate buffer, pH 6.5, at 4° C. If desired, the activated oligonucleotide may be further purified using an ethanol precipitation step.

In order to provide a label probe according to the method of the invention, the conjugation reaction can be conducted at various pHs and DNA:enzyme ratios to determine the desired conjugation conditions. The activated, purified bla3 is added to approximately 100 nmoles/ml of the affinity-purified alkaline phosphatase in 100 mM phosphate buffer, pH 7.2, or pH 7.8, at 4° C., at a DNA:enzyme ratio of 5:1, 25:1 or 100:1, and incubated for 30 min at 4° C. The reaction product is concentrated and washed into alkaline phosphatase storage buffer using a Centricon-30. The washing step is repeated three times to insure that unreacted DNA flows through the filter membrane and is minimized in the product.

If necessary, the alkaline phosphatase oligonucleotide conjugate may be further purified using, for example, ion exchange chromatography, hydrophobic chromatography, reverse phase chromatography, chromatofocusing or affinity chromatography. The ratio of label to DNA is determined using analytical gel electrophoresis. Enzymatic activity is determined using conventional assay techniques (see Landt et al., supra). The labeled reactive amines are determined by digesting the conjugated alkaline phosphatase and performing amino acid analysis using conventional techniques.

EXAMPLE 2

Effect of Sodium Dodecyl Sulfate on The Time Course of Chemiluminescence Generation Washed, concentrated alkaline phosphatase was prepared as described in Example 1.

Figure 3:
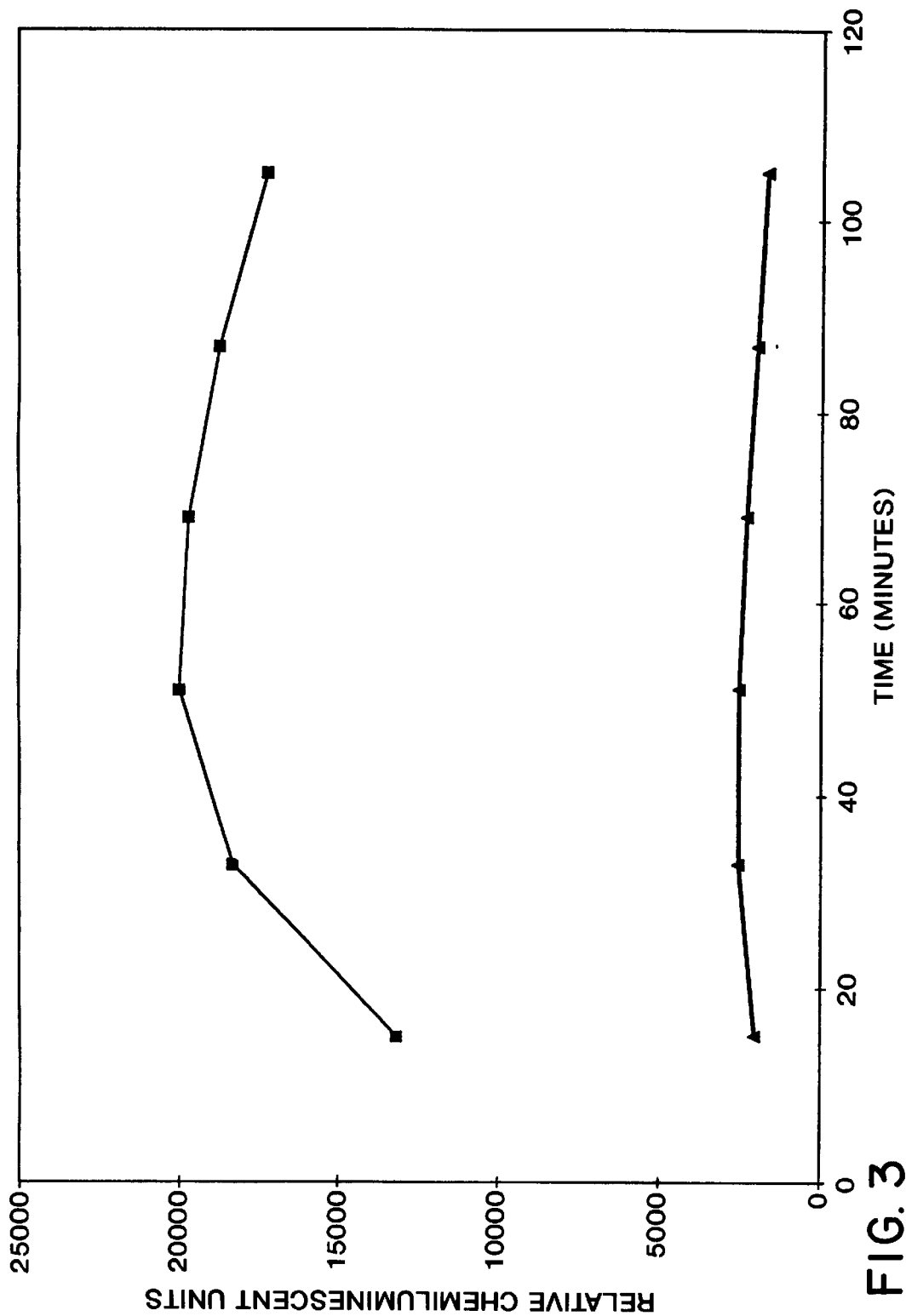
FIG. 3 is a graph illustrating the time course of the development of the chemiluminescent signal generated in the absence (solid triangles) or presence (solid squares) of the hydrophobic anionic enhancer sodium dodecyl sulfate in a soluble alkaline phosphatase assay.

The concentrated alkaline phosphatase was diluted to 1 attomole/microliter in substrate solution ((3-(2'-spiroadamantane)-4-methoxy-4-(3"-phosphoryloxy)-phenyl-1,2-dioxetane (disodium salt) (0.33 mM) (Lumigen® PPD, Lumigen, Inc., Southfield, Mich.) in 0.2 M 2-methyl-2-amino-1-propanol buffer, pH 9.6, with 0.88 mM $MgCl_2$ and 1.0 mg/ml 1-(tri-n-octylphosphoniummethyl)-4-(tri-n-butylphosphoniummethyl)benzene dichloride (see, EPA Publication No. 0630884)) or substrate solution with 0.03% SDS at 4° C. A fifty microliter aliquot of either solution was transferred to a luminometer and incubated at 37° C. The chemiluminescence generated in the solutions was monitored for the times indicated in FIG. 3. Enhancement of the alkaline phosphatase-catalyzed chemiluminescent signal by 0.03% SDS was observed at all time points tested.

EXAMPLE 3

Effect of Sodium Dodecyl Sulfate on Background Chemiluminescence

These experiments were conducted to determine the time course and concentration dependence of SDS-enhanced chemiluminescence and the effect of SDS on background chemiluminescence generated in the absence alkaline phosphatase.

A. Fifty microliters of substrate solution or substrate solution with 0.03% SDS prepared as described in Examples 1 and 2 were incubated at 37° C. in a luminometer and the chemiluminescence was monitored at the times indicated in FIG. 4A. The results depicted in FIG. 4A indicate that the effect of SDS to enhance chemiluminescent signal generation is specific for the enzyme-catalyzed signal.

B. Substrate solutions containing various concentrations of SDS or substrate solutions containing various concentrations of SDS and 1 attomole/microliter of alkaline phosphatase at 4° C. were prepared as described in Examples 1 and 2; the final concentration of SDS in each solution is indicated in FIG. 4B. Fifty microliter aliquots of each solution were incubated at 37° C. in a luminometer. Chemiluminescence was measured after 60 min. incubation. The results depicted in FIG. 4B show the peak enhancement of enzyme-catalyzed chemiluminescence generation at a given SDS concentration. In addition, these results show that, even at higher SDS concentrations, there is no effect of the enhancer in the absence of the enzyme.

EXAMPLE 4

Comparison of Effect of SDS and Brij-35 On Chemiluminescence Enhancement

The purpose of this experiment was to compare the effect of SDS, an anionic enhancer, with that of Brij-35, a non-ionic detergent, on alkaline phosphatase-generated chemiluminescence.

Alkaline phosphatase was prepared and conjugated to an oligonucleotide probe as described in Example 1.

Figure 5:
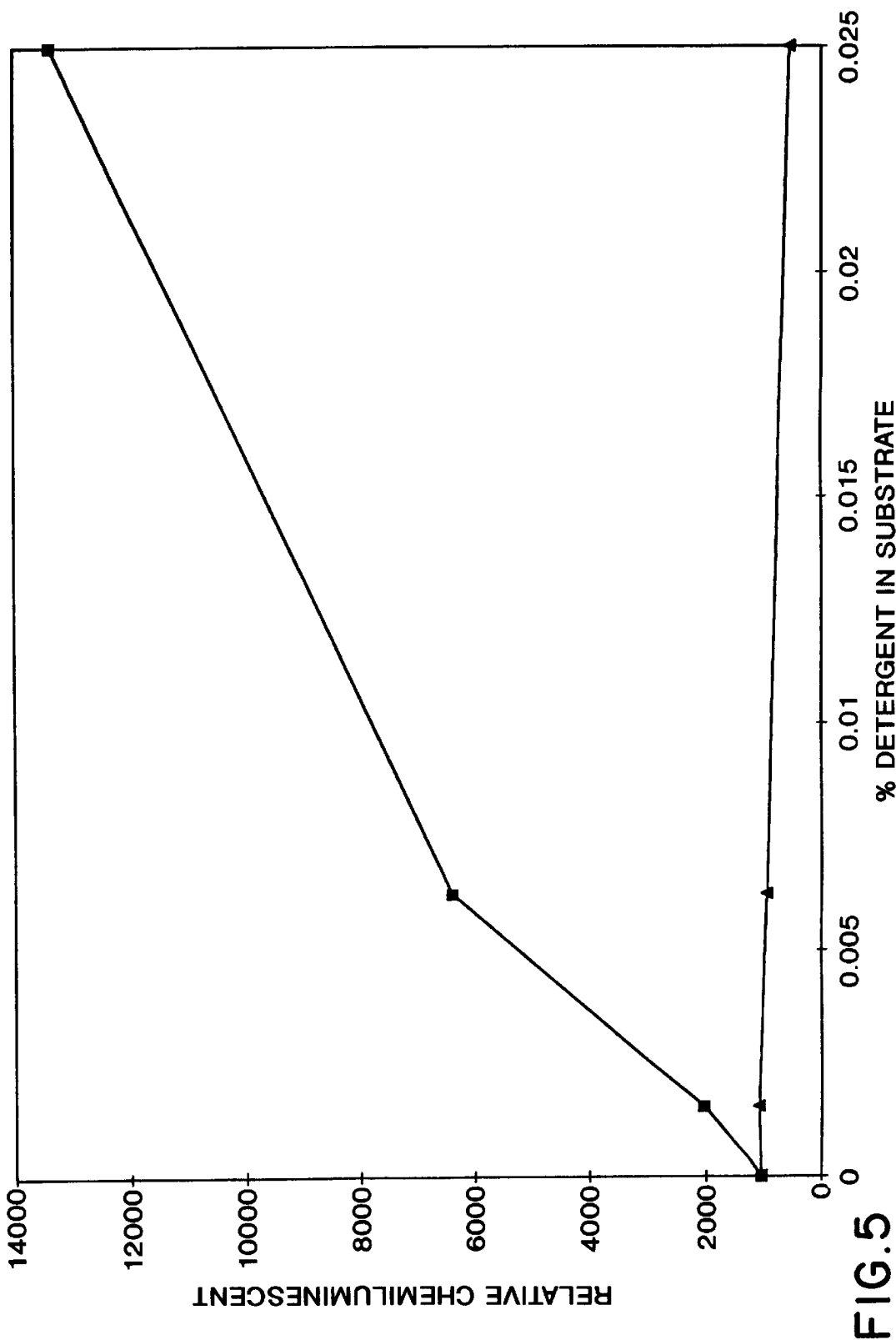
FIG. 5 is a graph showing the effect on of the concentration of sodium dodecyl sulfate (solid squares) and Brij-35 (solid triangles) on chemiluminescence generated in a soluble alkaline phosphatase assay wherein the alkaline phosphatase is conjugated to an oligonucleotide probe.

Oligonucleotide probe-conjugated alkaline phosphatase was diluted to 1 attomole/microliter alkaline phosphatase in substrate solution prepared as described in Example 2 and containing various concentrations of SDS or Brij-35 at 4° C.; the final concentration of SDS or Brij-35 is indicated in FIG. 5. Fifty microliter aliquots of each of the solutions were incubated at 37° C. in a luminometer and chemiluminescence was measured after 60 min. incubation.

The results of this experiment are depicted in FIG. 5 from which the enhancement of chemiluminescence by SDS and the absence of enhancement by Brij-35 can be seen. These results indicate that enhancement of alkaline phosphatase-generated chemiluminescence can be observed for soluble alkaline phosphatase whether or not it is conjugated to an oligonucleotide probe.

EXAMPLE 5

Detection of HIV Rev Response Element Probe #8730

This assay was done using the assay format diagrammed in FIG. 2 to detect the presence of a human immunodeficiency virus Rev response element probe ("the RRE probe") having the sequence (SEQ ID NO:2) 5'-TCCTGCTGCTCCCAAGAA-3'(SEQ ID NO:2). Extracts of MOLT-3 cells (ATCC CRL 1552), cytoplasmic or nuclear, were separated by centrifugation and spiked with various amount of the RRE probe to simulate quantitation of therapeutic antisense molecules in cells.

50 µl of amp diluent (50% horse serum, 0.05% sodium azide, 1.3% SDS, 5X SSC (20X SSC contains 175 gm/l sodium chloride and 88 g/l sodium citrate), 0.5 mg/ml proteinase K, 6 mM Tris-HCl, 0.05% Proclin 300® (Rolm-Haas) and 0.006 mM phenylmethylsulfonyl fluoride) containing 1 fmol/well of the capture extender "PSCP$^c$-target$^{c'}$" (5'-TTCTTGGGAGCAGCAGGACTCTTGGAAAGAA-AGTGAAGTG-3') (SEQ ID NO:3) was added to microtiter wells to which the capture probe "PSCPI" (5'-XCACTTCACTTTCTTTCCAAGAG-3') (SEQ ID NO:4), wherein X is as defined above, was bound. After 30 min at 37° C, the wells were washed 2-times with wash buffer A (0.1% SDS, 0.1X SSC, 0.05% sodium azide and 0.05% Proclin 300®). For the data shown in Tables 2 and 3, 50 µl of cellular extracts corresponding to 0, 24,000, 48,000 or 72,000 MOLT-3 cells containing 0, 2, 4, 6 or 8 fmol of the RRE probe was added to the wells. For the data shown in Table 3, 50 µl of cellular extracts corresponding to 0, 60,000, 120,000 or 180,000 MOLT-3 cells containing 0, 2, 4, 6 or 8 fmol of the RRE probe was added to the wells. The reaction mixture was incubated for 30 min at 37° C. The wells were washed two times with wash buffer A.

The alkaline phosphatase-bla3 label probe prepared according to the method described in Example 4 was added to amp diluent containing label extender bla3$^c$-target$^{c'}$(5'-GATGTGGTTGTCGTACTTTCCTGCT-GCTCCCAAGAA-3') (SEQ ID NO:5) in a final volume of 100 µl. The reaction mix was incubated for 30 min at 37° C. The reaction mix was diluted with label diluent and added to the wells at a final concentration of 5 fmol per 50 µl.

After incubating the reaction mix for 1 hr at 37° C., the microtiter wells were washed twice with wash buffer A and then twice with wash buffer D (0.1% Brij-35, 5 mM magnesium chloride, 0.1 M Tris-HCl, 0.01% sodium azide and 0.01% Proclin 300®). 50 µl (3-(2'-spiroadamantane)-4-methoxy-4-(3"-phosphoryloxy)-phenyl-1,2-dioxetane (disodium salt) (0.33 mM) (Lumigen® PPD, Lumigen, Inc., Southfield, Mich.) in 0.2 M 2-methyl-2-amino-1-propanol buffer, pH 9.6, with 0.88 mM $MgCl_2$ and 1.0 mg/ml 1-(tri-n-octylphosphoniummethyl)-4-(tri-n-butyl-phosphoniummethyl)benzene dichloride (see EPA Publication No. 0630884) and 0.03% SDS was added to the washed microtiter wells. The microtiter plates were incubated for 30 min at 37° C. and the signal generated was detected.

The data tabulated in Tables 2 and 3 indicate that the assay is linear over the range of the probe concentration tested, that the precision (as reflected by the %C.V.) is very high, and that the presence of a nuclear extract of MOLT-3 cells does not interfere with the detection of the probe.

TABLE 2

Addition of Cytoplasmic Extracts from MOLT-3 Cells

| PROBE (fmoles) | Avg. Signal | Standard Deviation | % C.V. | Signal - Noise |
|---|---|---|---|---|
| 0 Cells | | | | |
| 0 | 779.65 | 26.22 | 0.03 | 775.47 |
| 2 | 641.68 | 45.26 | 0.07 | 637.50 |
| 4 | 496.43 | 15.73 | 0.03 | 492.25 |
| 6 | 361.13 | 12.53 | 0.03 | 356.95 |
| 8 | 317.53 | 11.12 | 0.04 | 313.35 |
| 24,000 Cells | | | | |
| 0 | 823.48 | 10.10 | 0.01 | 818.99 |
| 2 | 680.75 | 47.93 | 0.07 | 676.26 |
| 4 | 480.45 | 18.41 | 0.04 | 475.96 |
| 6 | 369.28 | 16.43 | 0.04 | 364.79 |
| 8 | 279.28 | 17.08 | 0.06 | 274.79 |
| 48,000 Cells | | | | |
| 0 | 824.13 | 10.93 | 0.01 | 819.74 |
| 2 | 678.98 | 69.74 | 0.10 | 674.59 |
| 4 | 485.32 | 20.68 | 0.04 | 480.94 |
| 6 | 384.33 | 5.76 | 0.01 | 379.94 |
| 8 | 280.63 | 6.07 | 0.02 | 276.24 |
| 72,000 Cells | | | | |
| 0 | 787.48 | 24.82 | 0.03 | 782.08 |
| 2 | 666.93 | 64.31 | 0.10 | 661.53 |
| 4 | 481.65 | 29.15 | 0.06 | 476.25 |
| 6 | 389.28 | 10.63 | 0.03 | 383.88 |
| 8 | 292.98 | 13.27 | 0.05 | 287.58 |

TABLE 3

| PROBE | NUCLEAR EXTRACT ADDED (NUMBER OF CELLS) | | | |
|---|---|---|---|---|
| (fmoles) | 0 | 60,000 | 120,000 | 180,000 |
| 0 | 788.4 | 771.6 | 815.4 | 777.6 |
| 2 | 625.0 | 614.9 | 644.5 | 664.7 |
| 4 | 436.5 | 468.4 | 456.2 | 455.9 |
| 6 | 335.4 | 352.1 | 357.7 | 347.0 |
| 8 | 266.1 | 263.8 | 269.1 | 307.9 |

---

We claim:

1. A method for enhancing the chemiluminescence from a molecule that is triggerable to generate a chemiluminescent signal, which comprises:

(a) providing a molecule that is triggerable to generate a chemiluminescent signal, a dicationic surfactant, and a hydrophobic anionic enhancer having the formula $R^1X^-A^+$, wherein $R^1$ is a hydrophobic group that may be a substituted or unsubstituted hydrocarbon moiety selected from the group consisting of alkyl, cycloalkyl, alkenyl, alkynyl, aryl and aralkyl, $X^-$ is an anionic moiety covalently attached to the $R^1$ moiety, and $A^+$ is a countercation; and (b) activating the triggerable molecule to generate a chemiluminescent signal.

2. The method of claim 1, wherein the molecule that is triggerable to generate a chemiluminescent signal is a stable 1,2-dioxetane.

3. The method of claim 2, wherein $R^1$ is an alkyl group containing about 1 to about 20 carbon atoms.

4. The method of claim 2, wherein $R^1$ is an aralkyl group containing about 1 to about 20 carbon atoms.

5. The method of claim 2, wherein the hydrophobic anionic enhancer is selected from the group consisting of 3-[(3-cholamidopropyl)-dimethylammonio]-2-hydroxypropanesulfonate, 2-[N-cyclohexylamino)ethanesulfonate, 4-phenylbutyrate, chenodeoxycholate, taurodehydrocholate, taurolithocholate, deoxycholate, 4-sulfobenzoate, cholate, hexane sulfonate, taurocholate, glycocholate, glycodeoxycholate, benzene sulfonate, tauroursodeoxycholate, taurodeoxycholate, p-toluene sulfonate, taurochenodeoxycholate and sodium dodecyl sulfate.

6. The method of claim 5, wherein the hydrophobic anionic enhancer is sodium dodecyl sulfate.

7. The method of claim 5, wherein the hydrophobic anionic enhancer is p-toluene sulfonate.

8. The method of claim 2, wherein the dicationic surfactant has the structural formula $Z^-(R^2)_3B^+CH_2\text{-}Y\text{-}CH_2B^+(R^3)_3Z^-$ wherein B may be phosphorus, nitrogen or a combination thereof, Z is an anionic counterion and $R^2$ and $R^3$, which may be the same or different, and may be unsubstituted or substituted alkyl or aralkyl containing about 1 to about 20 carbon atoms and Y may be a dialkylenearyl, aryl, alkylene, alkenylene and alkynylene containing about 4 to about 20 carbon atoms.

9. The method of claim 8, wherein the B are phosphorus.

10. The method of claim 9, wherein $R^2$ and $R^3$ are alkyl.

11. The method of claim 10, wherein $R^2$ is octyl and $R^3$ is butyl.

12. The method of claim 11, wherein the hydrophobic anionic enhancer is sodium dodecyl sulfate.

13. A composition comprising:

(a) a molecule that is triggerable to generate a chemiluminescent signal;

(b) a dicationic surfactant; and (c) a hydrophobic anionic enhancer having the formula $R^1X^-A^+$, wherein $R^1$ is a hydrophobic group that may be a substituted or unsubstituted hydrocarbon moiety selected from the group consisting of alkyl, cycloalkyl, alkenyl, alkynyl, aryl and aralkyl, $X^-$ is an anionic moiety covalently attached to the $R^1$ moiety, and $A^+$ is a countercation.

14. The composition of claim 13, wherein the molecule that is triggerable to generate a chemiluminescent signal is a stable 1,2-dioxetane.

15. The composition of claim 14, wherein $R^1$ is an alkyl group containing about 1 to about 20 carbon atoms.

16. The composition of claim 14, wherein $R^1$ is an aralkyl group containing about 1 to about 20 carbon atoms.

17. The composition of claim 14, wherein the hydrophobic anionic enhancer is selected from the group consisting of 3-[(3-cholamidopropyl)-dimethylammonio]-2-hydroxypropanesulfonate, 2-[N-cyclohexylamino)ethanesulfonate, 4-phenylbutyrate, chenodeoxycholate, taurodehydrocholate, taurolithocholate, deoxycholate, 4-sulfobenzoate, cholate, hexane sulfonate, taurocholate, glycocholate, glycodeoxycholate, benzene sulfonate, tauroursodeoxycholate, taurodeoxycholate, p-toluene sulfonate, taurochenodeoxycholate and sodium dodecyl sulfate.

18. The composition of claim 17, wherein the hydrophobic anionic enhancer is sodium dodecyl sulfate.

19. The composition of claim 17, wherein the hydrophobic anionic enhancer is p-toluene sulfonate.

20. The composition of claim 14, wherein the dicationic surfactant has the structural formula $Z^-(R^2)_3B^+CH_2$-Y-$CH_2B^+(R^3)_3Z^-$ wherein B may be phosphorus, nitrogen or a combination thereof, Z is an anionic counterion and $R^2$ and $R^3$, which may be the same or different, and may be unsubstituted or substituted alkyl or aralkyl containing about 1 to about 20 carbon atoms and Y may be a dialkylenearyl, aryl, alkylene, alkenylene and alkynylene containing about 4 to about 20 carbon atoms.

21. The composition of claim 20, wherein the B are phosphorus.

22. The composition of claim 21, wherein $R^2$ and $R^3$ are alkyl.

23. The composition of claim 22, wherein $R^2$ is octyl and $R^3$ is butyl.

24. The composition of claim 23, wherein the hydrophobic anionic enhancer is sodium dodecyl sulfate.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 19
        ( D ) OTHER INFORMATION: /standard_name=
           " N4-(6-aminocaproyl-2-aminoethyl)cytosine"

( x i ) SEQUENCE DESCRIPTION: SEQ ID NO:1:

AAGTACGACA ACCACATCN                                    19

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TCCTGCTGCT CCCAAGAA                                    18

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TTCTTGGGAG CAGCAGGACT CTTGGAAAGA AAGTGAAGTG                40

( 2 ) INFORMATION FOR SEQ ID NO:4:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1
    (D) OTHER INFORMATION: /standard_name=
        " N4-(6-aminocaproyl-2-aminoethyl)cytosine"

(xi) SEQUENCE DESCRIPTION: SEQ ID NO:4:

NCACTTCACT TTCTTTCCAA GAG                    23

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GATGTGGTTG TCGTACTTTC CTGCTGCTCC CAAGAA       36